(12) United States Patent
Fournel et al.

(10) Patent No.: US 7,982,189 B2
(45) Date of Patent: Jul. 19, 2011

(54) SPECTROMETER FOR FLUID ANALYSIS

(75) Inventors: Johan Fournel, Robion (FR); Alain Lunati, La Fare les Oliviers (FR); Thierry Gergaud, Istres (FR)

(73) Assignee: SP3H, Aix-en-Provence (FR)

( * ) Notice: Subject to any disclaimer, the term of this patent is extended or adjusted under 35 U.S.C. 154(b) by 0 days.

(21) Appl. No.: 12/756,497

(22) Filed: Apr. 8, 2010

(65) Prior Publication Data
US 2010/0252737 A1 Oct. 7, 2010

Related U.S. Application Data

(63) Continuation of application No. PCT/IB2008/002563, filed on Sep. 26, 2008.

(30) Foreign Application Priority Data

Oct. 12, 2007 (FR) ...................... 07 07154

(51) Int. Cl.
G01J 5/02 (2006.01)
G01J 1/00 (2006.01)
G03F 7/20 (2006.01)

(52) U.S. Cl. ........... 250/339.07; 250/339.06; 250/495.1; 250/503.1; 250/504 R

(58) Field of Classification Search ............. 250/339.07, 250/339.06, 495.1, 503.1, 504 R
See application file for complete search history.

(56) References Cited

U.S. PATENT DOCUMENTS

| | | | |
|---|---|---|---|
| 4,989,942 A | 2/1991 | Koenigsberg et al. | |
| 6,137,108 A * | 10/2000 | DeThomas et al. | 250/339.07 |
| 6,560,038 B1 | 5/2003 | Parkyn, Jr. et al. | |
| 2004/0236198 A1 * | 11/2004 | Gritsenko | 600/323 |
| 2005/0140270 A1 | 6/2005 | Henson et al. | |
| 2007/0058389 A1 * | 3/2007 | Brukilacchio | 362/555 |
| 2007/0084990 A1 | 4/2007 | Coates | |
| 2009/0152475 A1 * | 6/2009 | Sasaki et al. | 250/492.1 |

FOREIGN PATENT DOCUMENTS

| | | |
|---|---|---|
| FR | 2 566 909 A1 | 1/1986 |
| FR | 2 583 164 A1 | 12/1986 |
| GB | 2 283 091 A | 4/1995 |
| JP | 2003066269 A * | 3/2003 |

OTHER PUBLICATIONS

European Search Report from the European Patent Office, dated Feb. 23, 2009, concerning counterpart International application No. PCT/IB2008/002563.
Written Opinion from the European Patent Office, dated Feb. 2, 2009, concerning counterpart International Application No. PCT/IB2008/002563.

* cited by examiner

*Primary Examiner* — David P Porta
*Assistant Examiner* — Mindy Vu
(74) *Attorney, Agent, or Firm* — Panitch Schwarze Belisario & Nadel LLP

(57) ABSTRACT

A spectrometer includes: a lighting device (LSRC) configured to generate a light beam covering a wavelength band, a probe configured so that the light beam coming from the lighting device interacts with a fluid to be analyzed, and a spectrum analyzing device configured to receive the light beam after it has interacted with the fluid to be analyzed, and to provide light intensity measurements for various ranges of wavelengths. The lighting device includes several light-emitting components (1a-1c) emitting light in various ranges of wavelengths, and a mixing optical component (3) fixed onto the emitting surface of the light-emitting components (1a-1g), to combine the light flows emitted by the light-emitting components into a resulting light beam covering the wavelength band, and guide the resulting light flow to the probe.

29 Claims, 6 Drawing Sheets

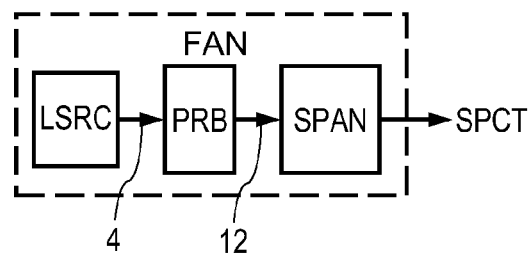
Fig. 1
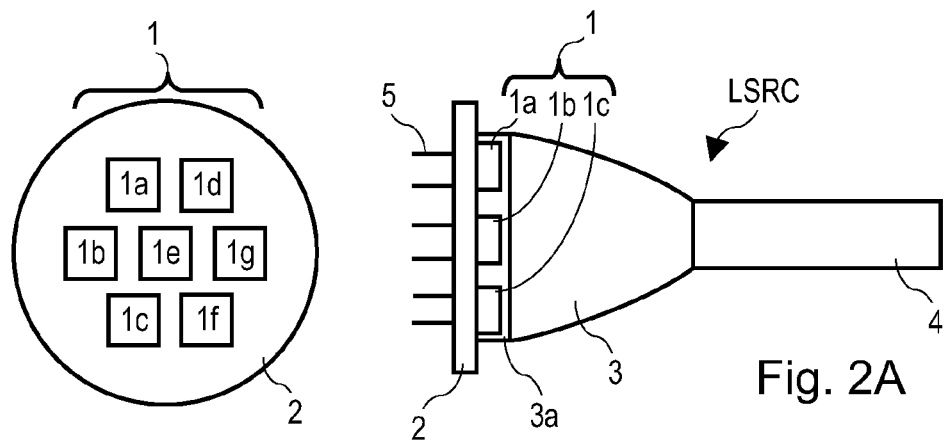
Fig. 2A
Fig. 2B
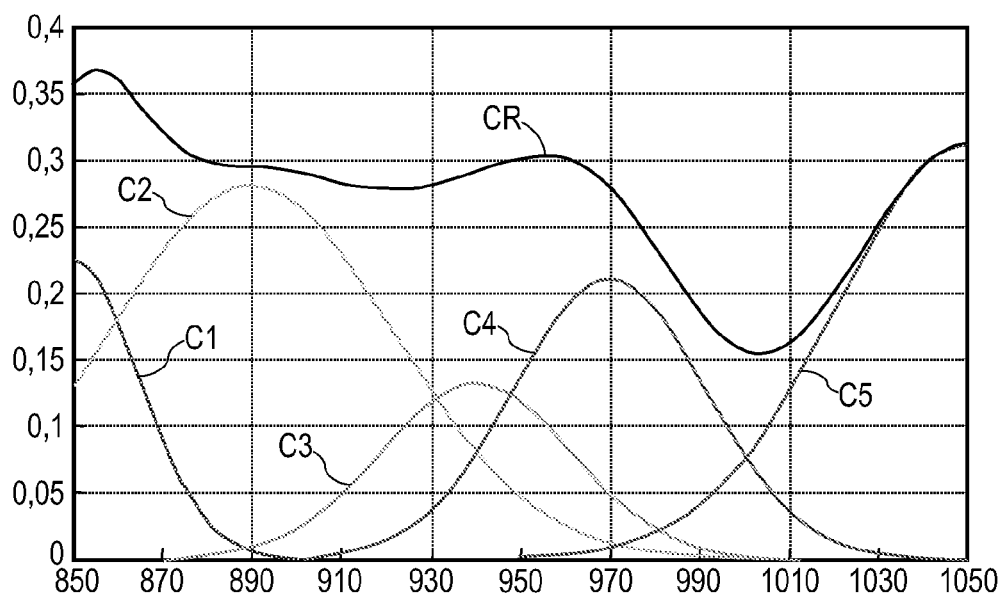
Fig. 3

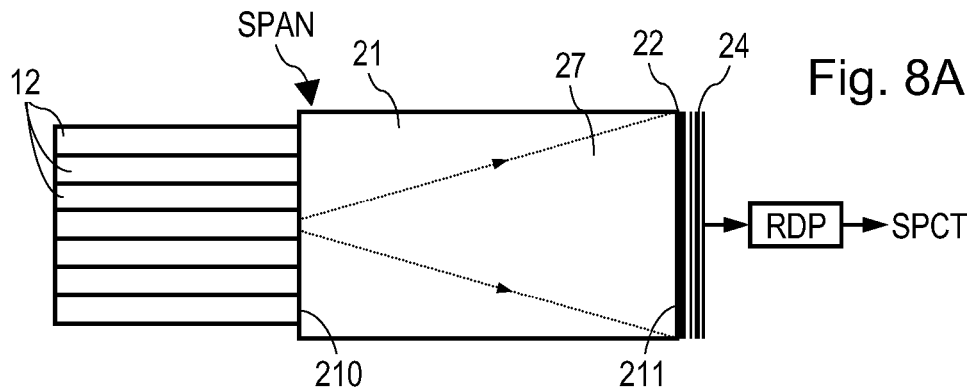
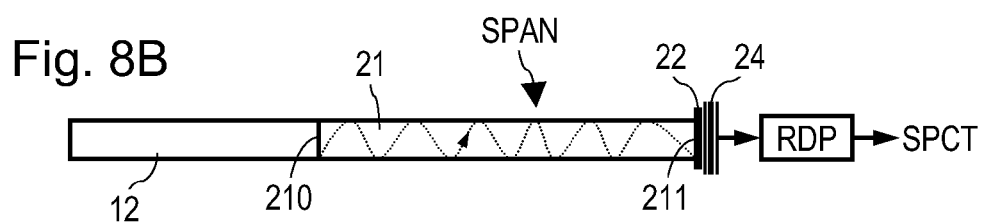
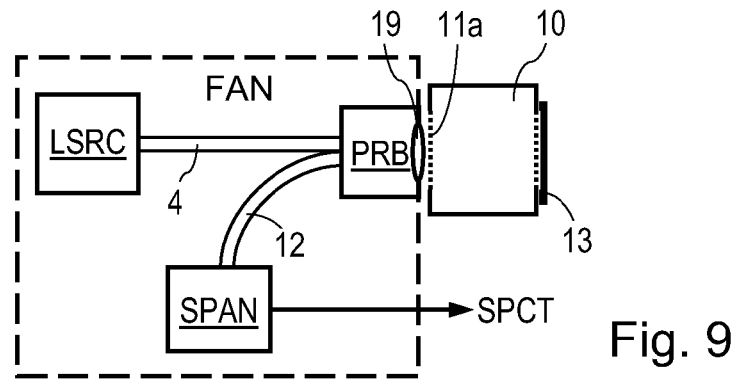
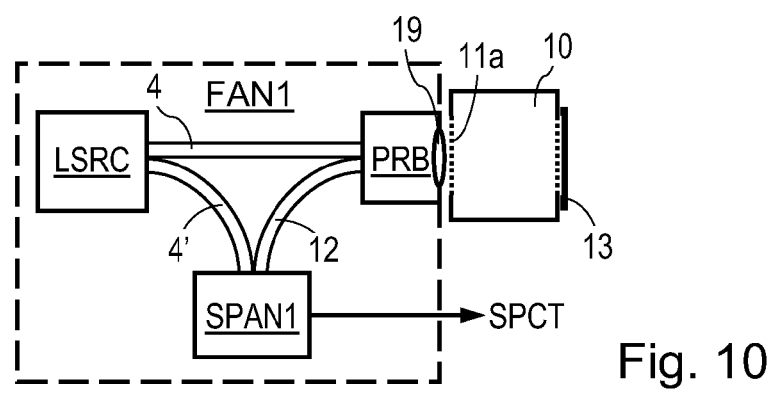

SPECTROMETER FOR FLUID ANALYSIS

CROSS-REFERENCE TO RELATED APPLICATIONS

This application is a Continuation of International Application No. PCT/IB2008/002563, filed Sep. 26, 2008, which was published in the French language on Apr. 16, 2009, under International Publication No. WO 2009/047605 A1 and the disclosure of which is incorporated herein by reference.

BACKGROUND OF THE INVENTION

The present invention relates to the analysis of fluids. The present invention relates more particularly to the qualitative analysis of fluids, and particularly of hydrocarbon- or biofuel-based fuels, ensuring the operation of a combustion engine such as those on motor vehicles.

Motor vehicles are more and more equipped with an electronic management system configured to optimize the operation of the engine according to different parameters measured by sensors. Such systems are generally configured to adjust the quantity of fuel injected into the engine, set the injection time, the ignition advance, the intake pressure and the recycling of exhaust gas, according, in particular, to the engine speed, the temperature of oil and coolant, and external parameters such as the atmospheric pressure and ambient temperature.

However, such optimization is limited by fluctuations in the quality of fuels. Indeed, although they are defined by standards, fuels are subject to significant variations in quality depending on the weather and the filling station. Fuels are generally characterized by physico-chemical parameters such as octane ratings and the vapor pressure for spark ignition engines, the cetane rating, the flashpoint and resistance to low temperatures for diesel engines, as well as the distillation curve, the density and the oxygenated compound content. It is thus estimated that the physico-chemical parameters of hydrocarbon-based fuels can vary by 15 to 40% or more, around standardized average values specified in standards.

Now, the operation of a combustion engine is optimized for standardized fuels. If the quality of the fuel taken at the pump is too different from the standardized fuel quality, such optimization is no longer done, and the engine will tend to consume more fuel and generate more polluting gas.

Therefore, it is desirable to determine the quality of fuel supplying the engine and to take the results obtained into account to manage the operation of the engine. For that purpose, near-infrared absorption spectrometry is suited to the qualitative assessment of a hydrocarbon or a hydrocarbon mix.

A standard spectrometer generating a fluid absorption spectrum generally comprises the following elements:

a light source covering at least one wavelength band in which the measurements must be taken, a device referred to as a "probe" in the following description, in which the light produced by the light source and the fluid to be analyzed interact, and a spectrum analyzing sensor which analyses the light at the output of the probe.

Such a spectrometer enables an absorption spectrum to be obtained in the form of a curve of $T=f(\lambda)$ type, indicating the quantity T of light having passed through the fluid to be analyzed according to the wavelength $\lambda$.

A spectrometer is characterized mainly by its spectrum analysis range (width and position of the spectra generated), its precision of analysis or the number of measurement points constituting the spectra supplied, its accuracy of measurement for the absorption value and its sensitivity, i.e. its capacity to measure low quantities of light.

Present-day spectrometers are generally very complex and thus very expensive, and are relatively large in size. In particular, present-day spectrometers comprise many optical components (lenses, filters, prisms, minors, diffraction gratings) separated by air spaces. The alignment of these components is critical for the spectrometer to function correctly. Therefore, present-day spectrometers, generally designed for laboratories, are not suited to the environment of a combustion engine or a motor vehicle. In particular, they are not designed to withstand the intense vibrations generated by the combustion engine or the motor vehicle. Indeed, between the light source and the spectrum analyzing device, the light beam passes through a significant number of optical components separated by air spaces. Each interface between an optical component and the air is a potential source of misadjustment or deterioration.

The light sources traditionally used in spectrometry (incandescent or metal vapor lamps, halogens, etc.) are not compatible with the requirements of robustness, service life and size required in an application on board a combustion engine or in a vehicle. The use of lasers must also be ruled out because the same number of lasers as measurement points in the desired spectrum would be necessary. The use of lasers must also be ruled out for reasons of service life, stability and robustness in a hostile environment.

Furthermore, French patent application publications No. FR 2 798 582 and FR 2 789 294 considered using light-emitting diodes associated with standard optical components.

U.S. Patent Application Publication No. 2007/0084990 describes a miniaturized spectrometer, integrating a source of energy and detectors in a single box which contains optical components for interfacing with the sample, and acquisition and processing circuits. The spectral selectivity is obtained by continuously variable optical filters or by a matrix filter. This device enables transmittance, absorption, turbidity and fluorescence to be measured. The document provides for using narrow- or broad-spectrum light sources such as white LEDs.

French patent application publication FR 2 583 164 describes a device comprising a light source associated with focusing optics to illuminate a fluid through an optical fiber. The light is collected from the fluid using another optical fiber which sends the light to a color separation device.

British published patent application GB 2 283 091 describes a liquid spectrum analyzing device for analyzing the spectrum of liquids comprising an optical fiber which sends a ray to a probe comprising a reflector and a passage for the liquid to be analyzed. The reflector reflects the ray in the fiber to an analyzing unit.

U.S. Patent Application Publication No. 2005/0140270 describes a light-emitting device comprising several sources of red, green or blue lights, such as LEDs. The light emitted by each source is concentrated by an element of an array of Concentrators, then sent by a respective light guide of a bundle of light guides.

U.S. Pat. No. 6,560,038 describes an optical coupler associated with an LED or a set of LEDs.

French patent application publication FR 2 566 909 describes a device for detecting a product in a liquid comprising a bundle of optical fibers a part of which sends light to the liquid, a mirror sunk in the liquid which reflects the light to the bundle of fibers, the other part of the bundle of fibers being linked to a detector.

U.S. Pat. No. 4,989,942 describes a device for analyzing a liquid comprising a light source sent by an optical fiber to a collimating lens. The light then passes through the liquid before being collected by another collimating lens. The collected light is then sent by an optical fiber to an analyzing device.

BRIEF SUMMARY OF THE INVENTION

It is therefore desirable to produce a fluid analyzing spectrometer capable of being installed on-board a combustion engine or in a motor vehicle.

This object is achieved by providing a spectrometer comprising a lighting device configured to generate a light beam covering a wavelength band, a probe configured so that the light beam coming from the lighting device interacts with a fluid to be analyzed, and a spectrum analyzing device configured to receive the light beam after it has interacted with the fluid to be analyzed, and to provide measurements depending on a quantity of light received for various ranges of wavelengths.

According to one embodiment, the lighting device comprises several light-emitting components each comprising an emitting surface and emitting light in various ranges of wavelengths included in the wavelength band, and a mixing optical component fixed onto the emitting surface of the light-emitting components, to combine the light flows emitted by the light-emitting components into a resulting light beam covering the wavelength band, and to guide the resulting light flow to the probe.

According to one embodiment, the mixing optical component has an input face receiving the light coming from the light-emitting components, an output face coupled to the lighting guide, and a shape having a substantially optimized revolution to focus and send as much light as possible from the light-emitting components to the probe.

According to one embodiment, the mixing optical component covers a light-emitting surface of each of the light-emitting components.

According to one embodiment, the mixing optical component is coupled by one or more optical fibers to a light-emitting surface of each of the light-emitting components.

According to one embodiment, the light beam produced by the lighting device covers a wavelength band between 700 nm and 1,100 nm.

According to one embodiment, the lighting device comprises several light-emitting components emitting light substantially in the same range of wavelengths.

According to one embodiment, the light-emitting components are light-emitting diodes.

According to one embodiment, the probe comprises an optical fiber illuminating light guide sending the light beam coming from the lighting device to the fluid to be analyzed, and an optical fiber collecting light guide coupled to the lighting guide and collecting at least partially the light beam having passed through the fluid to be analyzed and sending it to the spectrum analyzing device.

According to one embodiment, the collecting light guide comprises several collecting optical fibers spread around the illuminating light guide, and a reflector to send back the light beam after it has passed through the fluid to be analyzed to the collecting optical fibers through the fluid to be analyzed.

According to one embodiment, the reflector is produced so as to reflect each incident light ray of a light beam substantially in an opposite direction to that of the incident light ray with a slightly wider angle.

According to one embodiment, the reflector is of Scotchlite® type or safety reflector type with retro-reflecting prisms.

According to one embodiment, the reflector has the shape of a spherical shell centered substantially on the center of an output face of the illuminating light guide.

According to one embodiment, the probe comprises a converging lens arranged between the output of the illuminating light guide and the fluid to be analyzed.

According to one embodiment, the probe comprises a Y optical coupler to send the light beam at the output of the illuminating light guide into the fluid to be analyzed, and to send the light beam coming from the fluid to be analyzed into the collecting light guide, and a reflector to send back the light beam after it has passed through the fluid to be analyzed to the optical coupler through the fluid to be analyzed.

According to one embodiment, the reflector is produced so as to reflect each incident light ray of a light beam substantially in an opposite direction to that of the incident light ray.

According to one embodiment, the reflector is of Scotchlite® type or safety reflector type with retro-reflecting prisms.

According to one embodiment, the reflector has the shape of a spherical shell centered substantially on the center of an output face of the illuminating light guide.

According to one embodiment, the probe comprises a converging lens arranged between the coupler and the fluid to be analyzed.

According to one embodiment, the probe comprises a converging lens arranged between the output of the illuminating light guide and the fluid to be analyzed and a converging lens arranged between the collecting light guide and the fluid to be analyzed.

According to one embodiment, the spectrum analyzing device comprises a first light guide coupled to the probe and receiving the light beam after it has interacted with the fluid to be analyzed and diffusing it to a first set of light-sensitive cells through a first optical filtering device arranged to send each of the light-sensitive cells of at least one part of the set of light-sensitive cells, a part of the light beam covering a respective range of wavelengths included in the wavelength band.

According to one embodiment, the first light guide has the shape of a plate made of a transparent material, receiving the light beam coming from the fluid to be analyzed by an edge of the plate and diffusing it by spreading it to an opposite edge of the plate opposite which the first filtering device and the first set of light-sensitive cells are placed.

According to one embodiment, the collecting light guide is coupled to the first light guide to send it the light beam.

According to one embodiment, the spectrum analyzing device comprises a strip of photodetectors comprising the first set of light-sensitive cells, which is fixed onto the edge of the plate through the first filtering device.

According to one embodiment, the first filtering device comprises a filter of the spectrum transmission interference type linearly variable over its length.

According to one embodiment, the filtering device covers a wavelength band between 700 nm and 1,100 nm.

According to one embodiment, the spectrum analyzing device comprises a second light guide taking a part of the light beam directly at the output of the lighting device and sending the part of the light beam to a second set of light-sensitive cells through a second optical filtering device arranged to send each of the light-sensitive cells a part of the light beam covering a respective range of wavelengths included in the wavelength band.

According to one embodiment, the second light guide has the shape of a plate made of a transparent material, receiving a part of the light beam coming from the lighting device by an edge of the plate and diffusing it by spreading it to an opposite edge of the plate opposite which the second filtering device and the second set of light-sensitive cells are placed.

According to one embodiment, the device comprises an optical fiber light guide coupled to the second light guide to send the light beam coming from the lighting device to the second light guide.

According to one embodiment, the spectrum analyzing device comprises a strip of photodetectors comprising the first and the second sets of light-sensitive cells, which is fixed onto the edge of the plates of the first and second light guides through the first and second filtering devices.

According to one embodiment, the second filtering device comprises a filter of the spectrum transmission interference type linearly variable over its length.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 represents in block form some functions of a spectrometer adapted to the environment of a combustion engine or a motor vehicle, FIG. 2A is a side view of a lighting device of the spectrometer, FIG. 2B is a front view of light sources of the lighting device, FIG. 3 represents in the form of curves some examples of emission spectra of light sources of the lighting device, FIG. 8A is a top view of a spectrum analyzing device of the spectrometer, FIG. 8B is a side view of the spectrum analyzing device, FIG. 9 represents in block form the arrangement of the spectrometer, FIG. 10 represents in block form an alternative arrangement of the spectrometer.

DETAILED DESCRIPTION OF THE INVENTION

Figure 4:
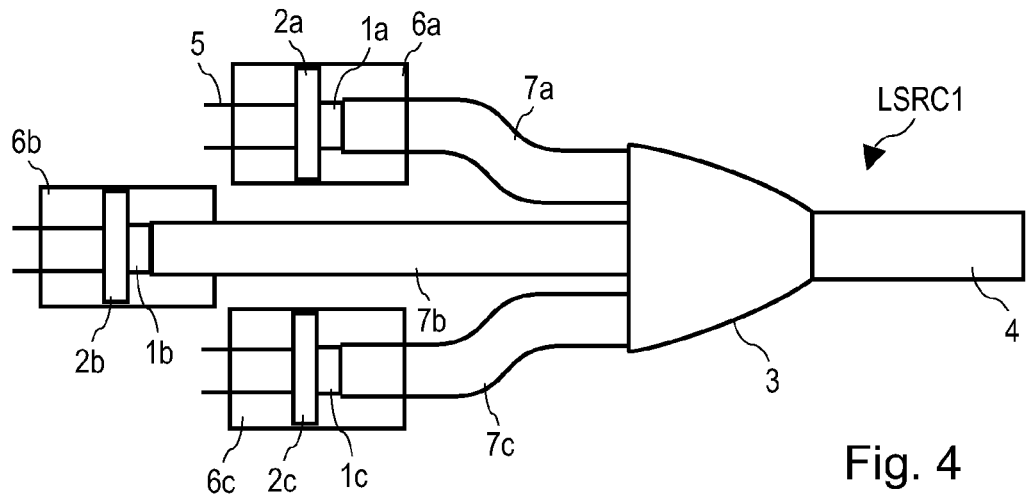
FIG. 4 is a side view of an alternative embodiment of the lighting device of the spectrometer.

In the following description of the figures, the same elements have the same references.

FIG. 1 represents a spectrometer FAN to analyze a fluid. The device FAN comprises:

a lighting device LSRC covering at least one wavelength band in which spectrometry measurements must be taken, a probe PRB configured so that the light produced by the lighting device LSRC interacts with the fluid to be analyzed, a spectrum analyzing sensor SPAN which analyses the light at the output of the probe, and optical elements 4, 12 configured to guide the light beam between the source and the probe and between the probe and the sensor.

The fluid to be analyzed may be a gas or a liquid, and in particular a hydrocarbon or a hydrocarbon mix, or even a mix of hydrocarbons and biofuels.

FIGS. 2A and 2B represent one embodiment of the lighting device LSRC. The lighting device LSRC comprises a light source 1 mounted onto a medium 2, and connected to a source of energy (not represented) by connecting pins 5. The light source 1 comprises for example a light-emitting component of light-emitting diode (LED) type. The medium 2 may comprise a printed circuit wafer onto and to which the light-emitting component 1 is mounted and connected.

An optical fiber 4 is coupled to the light-emitting surface of the component 1 to send the light generated towards the probe PRB.

If the wavelength band to be covered to take the spectrometric measurements cannot be covered by a single light-emitting component, several light-emitting components 1a-1g in various ranges of wavelengths can be mounted onto the medium 2.

Thus, current light-emitting diodes have an emission wavelength spectrum of several tens of nanometers in width. Several light-emitting diodes are therefore needed if the spectrum to be covered extends over several hundred nanometers. For example, the lighting device can thus cover a spectrum of wavelengths ranging between 700 and 1,100 nm.

The lighting device LSRC then comprises an optical component 3 configured to mix the light coming from each of the light-emitting components 1a-1g and to guide the mixed light towards the optical fiber 4. The optical component 3 can be made of a transparent material in the spectrum of measurement wavelengths of the analyzer. The optical component 3 is for example of TIR-type (Total Internal Reflection), so as to send the light energy produced by the light-emitting components 1a-1g to the optical fiber 4 with optimum efficiency. The component 3 has an input face covering all the light-emitting components 1a-1g and an output face having substantially the same shape and dimensions as the input face of the fiber 4. The revolution of the component 3 is substantially conical, and its generator is optimized to send the optical fiber 4 as much light as possible from the light-emitting components 1a-1g. The component 3 is fixed onto the components 1a-1g and onto the medium 2 for example by means of a layer of transparent glue 3a fully covering the components 1a-1g. The optical fiber 4 can also be fixed onto the component 3 by means of transparent glue.

FIG. 3 represents six curves of lighting power according to the wavelength, corresponding to the emission spectra C1-C5 of various light-emitting diodes, and to the resulting spectrum CR obtained after the optical component 3 has combined the spectra C1-C5. Each emission spectrum C1-C5 has substantially the shape of a Gauss curve. The spectra C1-C5 have respective maximum values in the vicinity of 850 nm, 890 nm, 940 nm, 970 nm, and 1,050 nm. As these maximum values are not identical, the lighting device LSRC may comprise several light-emitting components having a substantially identical emission spectrum so that the resulting spectrum CR is as flat as possible (constant power) in the wavelength band to be covered.

FIG. 4 represents another embodiment of the lighting device. In FIG. 4, the lighting device LSRC1 comprises several lighting elements 6a, 6b, 6c each comprising a light-emitting component 1a, 1b, 1c mounted onto a medium 2a, 2b, 2c, and coupled directly to an optical fiber 7a, 7b, 7c. The light-emitting surface of each component 1a, 1b, 1c is thus in contact with the input surface of the optical fiber 7a, 7b, 7c. The output surface of each optical fiber is coupled to an optical component such as the optical component 3 previously described. The optical fibers 7a, 7b, 7c can be fixed onto the components 1a, 1b, 1c or onto the media 2a, 2b, 2c and onto the component 3 by means of transparent glue.

Here again, the mixing optical component 3 may be omitted. The optical fibers coming from the diodes are then grouped together into a bundle of optical fibers sending the light beam coming from the lighting device to the probe PRB.

It shall be noted that in the embodiment in FIG. 4, the diodes 1a-1c can also be mounted onto the same medium 2 as shown in FIGS. 2A, 2B.

Figure 5A:
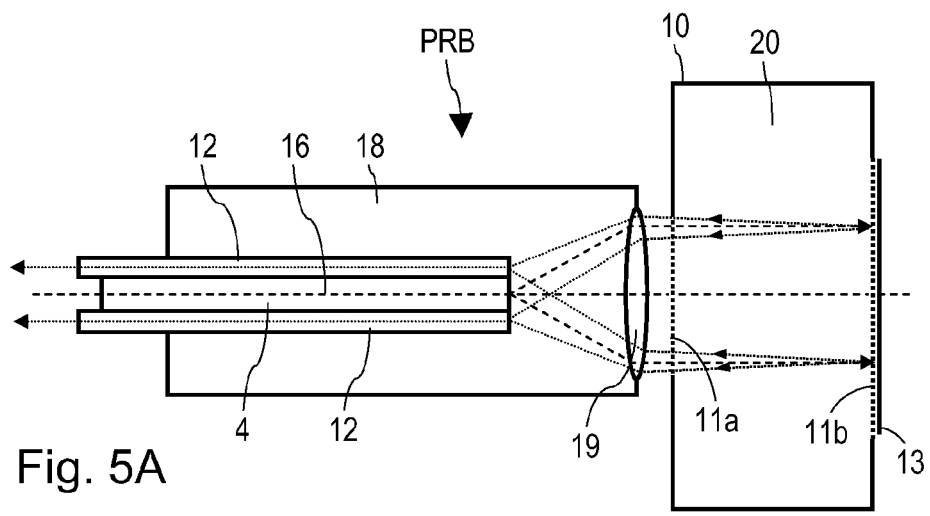
FIG. 5A is a side view of a transmission probe for transmitting a light beam generated by the lighting device to the fluid to be analyzed.

FIG. 5A represents the probe PRB. The probe PRB comprises several optical fibers 4, 12 arranged in a bundle and a converging lens 19.

Figure 5B:
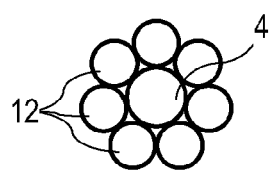
FIG. 5B is a cross-section of an arrangement of optical fibers in the probe.

FIG. 5B represents an example of arrangement of the fibers in the bundle. On FIG. 5b, the bundle comprises a central optical fiber, referred to as the lighting optical fiber, corresponding to the fiber 4 coming from the lighting device LSRC, and lateral optical fibers 12, referred to as collecting optical fibers, arranged around the central fiber 4. The central optical fiber 4 may have a different diameter, for example greater than that of the lateral fibers 12. In the example in FIG. 5B, the probe PRB comprises seven fibers 12.

The lens 19 is coupled to the fibers 4, 12 so that its optical axis 16 substantially coincides with that of the light beam at the output of the central fiber 4, the centre of the output face of the fiber 4 being located in the vicinity of the focal point of the lens. The diameter of the lens 19 is such that a light beam sent by the fiber 4 is entirely sent by the lens to infinity, given the angle of the light beam at the output of the fiber 4. All the fibers 4, 12 and the entire lens 19 can be housed in a box 18.

The fluid to be analyzed is arranged on the route of the light beam at the output of the lens 19. For this purpose, a pipe or a tank 10 containing the fluid to be analyzed 20 comprises a transparent window 11a and a flat reflector 13, arranged on the route of the light beam at the output of the lens 19. The reflector 13 is arranged perpendicular to the optical axis 16, so that the light beam passes through the fluid to be analyzed 20 and is reflected towards the fibers 4 and 12 through the lens 19. The light beam thus passes twice through the fluid to be analyzed between the window 11a and the reflector 13.

The reflector 13 is of retro-reflective type to the light source, i.e. reflecting each incident light ray in the opposite direction to that of the incident light ray with a slight deflection so that the reflected beam is focused by the lens 19 on a surface area larger than the fiber 4, covering in particular the input face of the fibers 12.

For example, the reflecting surfaces marketed under the brand name Scotchlite® by the company 3M have this property: a light beam arriving on such a surface leaves it in an opposite direction with a slightly wider angle. This type of surface is used for example to manufacture retro-reflecting safety clothing. For this purpose, the reflecting surface comprises transparent microbeads stuck onto a medium and half of the surface of which turned toward the medium is covered with a reflecting layer.

Safety reflectors with retro-reflecting prisms also have the same property.

This property offsets an alignment fault between an axis perpendicular to the reflector 13 and the optical axis 16 of the lens 19.

The pipe or tank 10 may comprise a second transparent window 11b positioned on the route of the light beam, onto which the reflector 13 is fixed.

It will be understood that the transparent window 11a may be combined with the lens 19.

Figure 6:
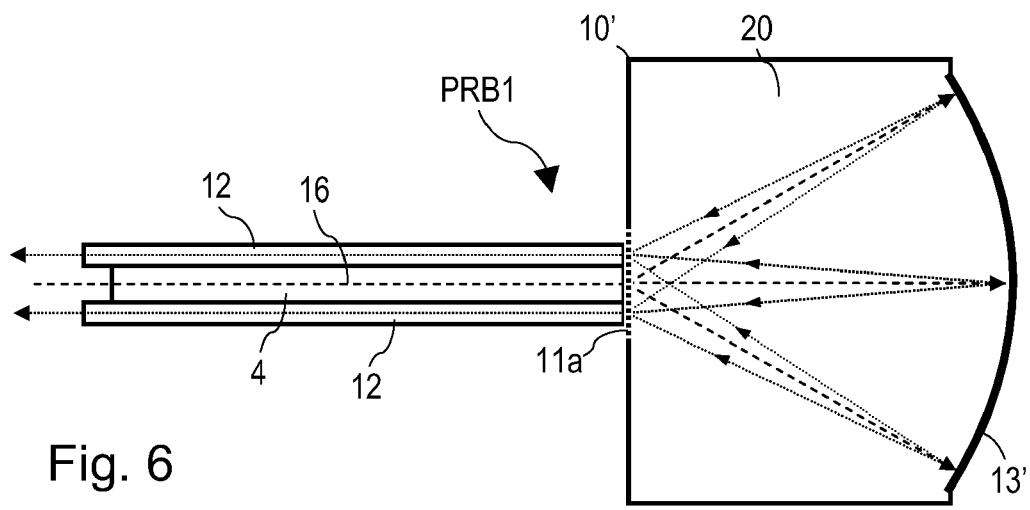
FIG. 6 is a side view of an alternative embodiment of the probe.

FIG. 6 represents another embodiment of the probe. In this embodiment, the probe PRB1 differs from the one represented in FIG. 5A due to the absence of the lens 19. The tank or pipe 10' containing the fluid to be analyzed 20 comprises, as in FIG. 5A, a transparent window 11a letting the light beam coming from the fiber 4 to enter the fluid to be analyzed. Opposite the transparent window 11a, a reflector 13' in the form of a spherical shell centered substantially on the centre of the output face of the fiber 4 is provided. Thus, all the rays of the light beam at the output of the fiber 4 travel a route of substantially the same length in the fluid to be analyzed 20.

The reflector 13' has a retro-reflecting surface such that it enlarges the reflected beam to cover the input faces of the fibers 12.

The entire beam coming from the fiber 4 thus enters the pipe or tank 10' via the transparent window 11a and is reflected by the reflector 13 towards the fibers 4, 12.

The reflector 13' is once again arranged either inside the pipe or tank, or on a transparent window in the form of a spherical shell provided in the pipe or the tank 10'.

Provision can also be made to interlock the ends of the fibers 4, 12 with the reflector 13' and to sink them into the fluid to be analyzed 20.

Figure 7:
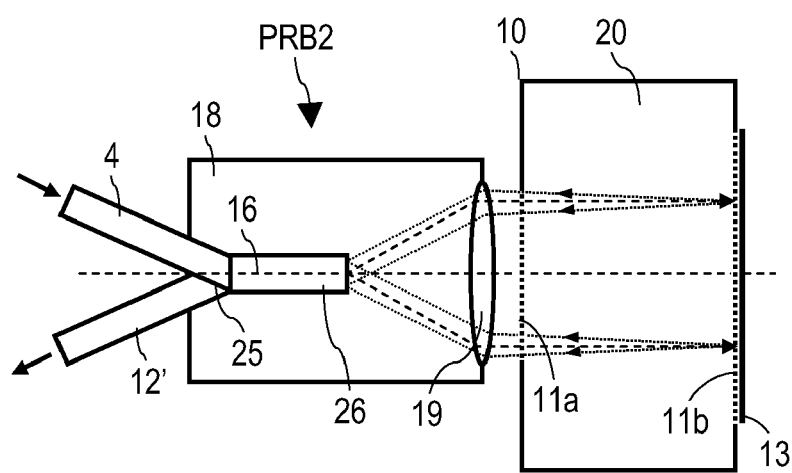
FIG. 7 is a side view of another alternative embodiment of the probe.

FIG. 7 represents another embodiment of the probe. In this embodiment, the probe PRB2 differs from the one represented in FIG. 5A due to the presence of a Y coupler 25 and a single collecting fiber 12'. The probe PRB2 comprises a single fiber 26 sending the light beam to the fluid to be analyzed 20 and capturing the light beam coming from the latter. The coupler 25 is configured to separate the light beams according to their direction of propagation and thus to direct the beam coming from the lighting device LSRC or LSRC1 towards the fiber 26 and the fluid to be analyzed, and the light beam having passed through the fluid to be analyzed is sent by the fiber 26 towards the optical fiber 12' coupled to the input of the spectrum analyzing sensor SPAN. The optical fibers 4, 26 and 12' can be fixed onto the coupler 25 by means of transparent glue.

It will be understood that, as described above with reference to FIG. 6, the lens 19 in the embodiment in FIG. 7 may be removed. In this case, a reflector in the form of a spherical shell like the one presented in FIG. 6 is used.

FIGS. 8A, 8B represent one embodiment of the spectrum analyzing sensor SPAN. The sensor SPAN comprises a light guide 21, an optical filter 22 and a light-sensitive sensor 24. The light guide 21 is made of a transparent material, for example glass, and has the shape of a substantially parallel-epipedal plate, of a low thickness substantially equal to or greater than the diameter of the optical fibers 12 coming from the probe PRB. Each collecting optical fiber 12 is fixed onto a lateral face or edge 210 of the plate, for example using transparent glue.

The sensor 24 comprises a set of light-sensitive cells which can be arranged as a strip, and covered by the filter 22. The strip of light-sensitive cells with the filter 22 covers the lateral face or edge 211 of the guide 21 opposite the lateral face or edge 210 onto which the collecting optical fibers 12 are fixed.

The sensor 24 is for example of the CMOS-sensor type comprising a plurality of light-sensitive elements, for example 64 or 128 light-sensitive cells. The filter 22 comprises one filter element per light-sensitive cell, configured to send light rays located in a respective range of wavelengths of the wavelength band to be analyzed, so that each light-sensitive cell supplies the value of a point on the curve of the spectrum to be generated. The output signal of each cell is a measurement of a quantity of light having passed through the fluid to be analyzed for the range of wavelengths sent to the cell by the filter 22.

The measurements thus taken by the cells are sent to a signal processing device RDP configured to generate a spectrum of the shape I=f($\lambda$) indicating the quantity of light I sent by the fluid to be analyzed according to the wavelength $\lambda$. The signal processing device is also configured to deduce from the absorption spectrum thus generated certain characteristics SPCT of the fluid passed through by the light beam coming from the lighting device LSRC.

The material constituting the guide 21 has a refraction index such that all the light rays introduced by the edge 210 are reflected by the walls of the guide and only leave the latter via the opposite edge 211. The light beams at the output of the collecting optical fibers 12 are thus fully sent to the filter 22. The geometry thus chosen for the guide 21 enables the light beams coming from the probe PRB to be spread in a substantially homogeneous manner over the entire surface of the filter 22.

The guide 21 has for example a thickness of about 1 mm and a width of approximately 7 mm for seven collecting fibers 12, each with a diameter of 1 mm. The length of the guide 21 is for example determined according to the angle of the light beam at the output of the fibers 12 in the guide 21, so that the beam 27 at the output of the collecting fiber fixed in the middle of the width of the guide 21 covers the entire filter 22.

The filter 22 can be of the spectrum transmission interference type linearly variable over its length, letting through each wavelength component of the light beam received in a position depending on its wavelength, along the width of the output face (edge) 211 of the guide 21. Therefore, each light-sensitive cell of the sensor 24 receives light rays located in a distinct wavelength band, and two adjacent cells of the sensor receive light rays located in two contiguous ranges of wavelengths.

It will be understood that, if the probe comprises a single collecting optical fiber like the fiber 12' in FIG. 7, a single fiber is fixed onto the input face (edge) 210 of the light guide 21, preferably in the middle of this face.

FIG. 9 represents the arrangement of the different components previously described in the spectrometer FAN. In FIG. 9, the lighting device LSRC is linked to the probe PRB (or PRB1, PRB2) through the optical fiber 4. In the case of the probe PRB or PRB2, the lens 19 is placed opposite the transparent window 11a and the reflector 13 on the pipe or tank 10 containing the fluid to be analyzed 20. The probe PRB (or PRB1, PRB2) is linked to the spectrum analyzing sensor SPAN through the optical fibers 12 (or the optical fiber 12' in the case of probe PRB2).

FIG. 10 represents another embodiment of the spectrometer. In FIG. 10, the spectrometer FAN1 differs from the spectrometer FAN in that it comprises a spectrum analyzing device SPAN1, and an optical fiber 4' linking the output of the lighting device LSRC to the device SPAN1.

On FIGS. 9 and 10, the lighting device can also be the device LSRC1.

Figure 11:
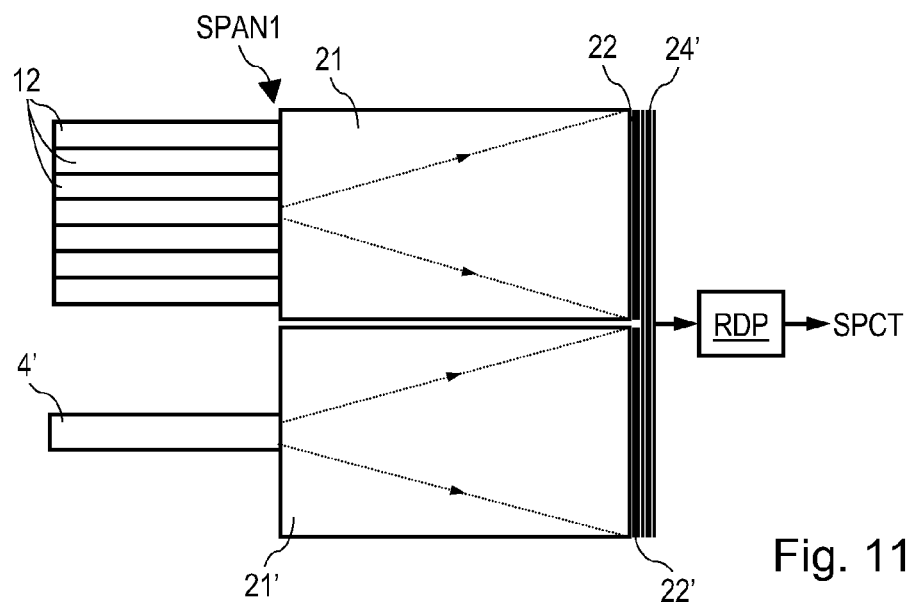
FIG. 11 is a top view of the spectrum analyzing device of the spectrometer represented in FIG. 10.

FIG. 11 represents the spectrum analyzing sensor SPAN1 of the spectrometer FAN1. In FIG. 11, the spectrum analyzing sensor SPAN1 comprises two sensors such as the one SPAN represented on FIGS. 8A, 8B. Thus, the sensor SPAN1 comprises two light guides 21, 21' and two optical filters 22, 22' and two light-sensitive sensors. The input face of the guide 21 is coupled to the optical fibers 12 and the input face of the guide 21' is coupled to the optical fiber 4'.

The optical fiber 4' can be connected to the lighting device LSRC (or LSRC1) through an optical fiber coupler (not represented) known per se, capable of sending the light beam at the output of the mixing component 3 substantially without any loss and in a balanced manner to the two optical fibers 4, 4'.

In the example in FIG. 11, the sensor SPAN1 comprises a single light-sensitive sensor 24 comprising two times more light-sensitive cells, for example 128 or 256, to analyze the light beams sent by the two guides 21, 21', each associated with a filter 22, 22'.

The light sent directly from the lighting device LSRC by the fiber 4' is analyzed through the filter 22' and indicates for each wavelength $\lambda$ the quantity of light R($\lambda$) emitted by the lighting device.

The light sent from the probe PRB by the collecting fibers 12 indicates for each wavelength $\lambda$ the quantity of light t($\lambda$) having passed through the fluid to be analyzed.

Therefore, the device SPAN1 can constitute a corrected transmission spectrum taking into account any fluctuations in the light beam coming from the lighting device, of the shape T($\lambda$)=t($\lambda$)/R($\lambda$).

Figure 12:
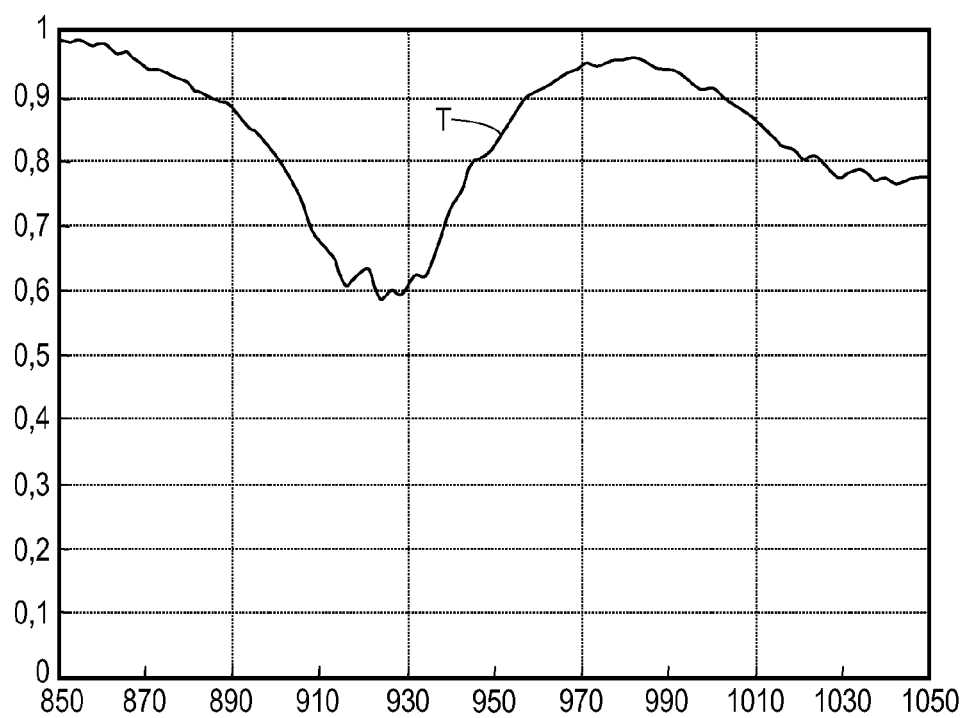
FIG. 12 represents an example of a fluid absorption curve obtained by the spectrum analyzing device.

FIG. 12 represents an example of such an absorption spectrum T between the wavelengths equal to 850 nm and 1,050 nm, T being substantially equal to 1 when the fluid is totally transparent at the corresponding wavelength $\lambda$ and substantially equal to 0 when the fluid is totally impenetrable at the corresponding wavelength $\lambda$.

Figure 13:
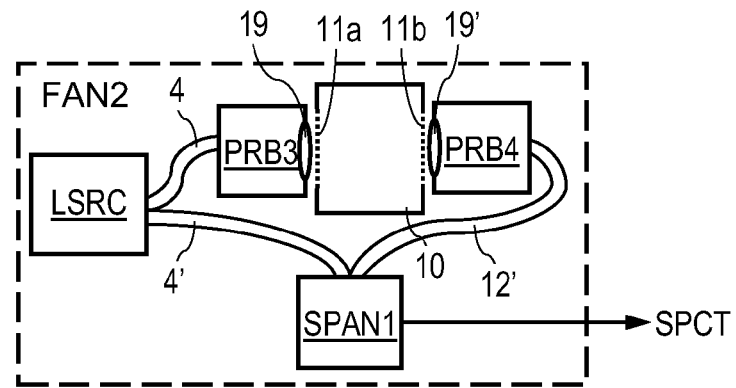
FIG. 13 represents in block form a second alternative arrangement of the spectrometer.

FIG. 13 represents another embodiment of the spectrometer. In FIG. 13, the spectrometer FAN2 differs from the device FAN1 due to the presence of a modified probe comprising two parts PRB3, PRB4, i.e. one probe part PRB3 connected to the lighting device LSRC and one probe part PRB4 connected to the analyzing sensor SPAN1. The two probe parts PRB3, PRB4 are placed on either side of the pipe or tank 10 in front of transparent windows 11a, 11b, the part PRB 1 being connected to the fiber 4 to send the light beam generated by the lighting device to the fluid to be analyzed 20, and the part PRB2 receiving the light beam after it has passed through the fluid to be analyzed, and sending it to the fiber 12'.

It will be understood that the lighting device LRSC1 may also be used in the device FAN2.

Figure 14:
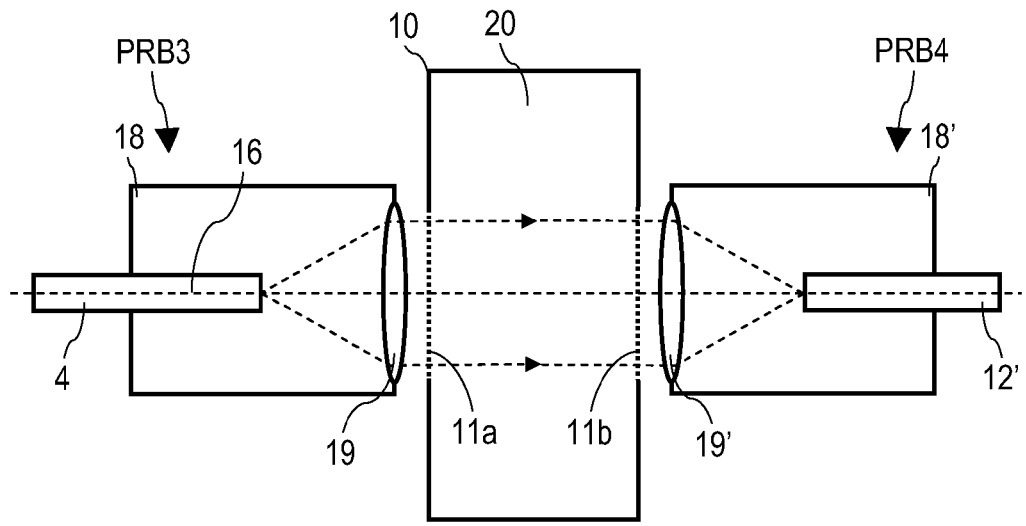
FIG. 14 is a side view of the probe of the spectrometer represented in FIG. 13.

FIG. 14 represents the two probe parts PRB3, PRB4. The part PRB3 comprises the box 18 and the lens 19 of the probe PRB. The part PRB4 comprises a lens 19' which focuses the light beam having passed through the fluid to be analyzed 20 and the window 11b, on the centre of the input face of the fiber 12'. The entire lens 19' and the end of the fiber 12' can be mounted into a box 18'. In this arrangement, the fibers 4, 12' and the lenses 19, 19' are coupled to each other, so that the axis of the light beam at the output of the fiber 4 coincides with the optical axis 16 of the lenses 19, 19' and the input axis of the fiber 12'.

It shall also be noted here that the lenses 19, 19' can constitute the transparent windows 11a, 11b.

It will be understood that the optical fibers 4, 4', 12, 12' described above, linking up the lighting device LSRC, LSRC1, the probe PRB, PRB1-PRB4 and the analyzing device SPAN, SPAN1, can be replaced by bundles of fibers.

The different optical elements of the spectrometer FAN, FAN1, FAN2 are aligned during the assembly of these elements and their connection by optical fibers. The assembly can be done so as to form a single block without any air or vacuum between the optical components by using optical fibers, which also renders the device insensitive to vibrations. Thus, all the components and optical fibers of the device can for example be sunk in a resin, for example of potting type, suited to withstand aggressive environments.

In addition, the spectrometer FAN, FAN1, FAN2 uses only low-cost components with a long service life, and its composition makes it compatible with a mass production process. Therefore, the spectrometer proves to be perfectly suited to the environment of a combustion engine and a motor vehicle.

It will be understood by those skilled in the art that various alternative embodiments and (various) applications of the present invention are possible. In particular, the present invention is not limited to the use of optical fibers to connect the different elements (lighting device, probe and spectrum analyzing device) of the spectrometer. The present invention is not limited either to a device comprising a single optical fiber linking the lighting device to the probe and to the spectrum analyzing device, and to one or seven optical fibers linking the probe to the spectrum analyzing device. Indeed, these connections can also be produced by light guides made up of a bundle of optical fibers.

The present invention may also comprise a lighting device without any mixing optical component 3. Indeed, this component can be omitted if an optical fiber or a bundle of optical fibers having an input face covering all the light-emitting diodes is used. The optical fiber or the bundle can then be fixed onto the diodes by means of a layer of transparent glue into which the diodes are sunk. In the absence of the mixing optical component 3, the light beams located in various ranges of wavelengths generated by the light-emitting diodes 1a-1g are mixed in the fluid to be analyzed, then collected by the optical fibers 12 or the fiber 12' and the optical guide 21. In the embodiment in FIG. 11, the light beams sent directly to the spectrum analyzing device SPAN1 are mixed in the fiber 4' and in the light guide 21'.

The present invention is not limited either to a light guide 21, 21' in the form of a plate. Other shapes may also be suitable depending on the shape and the distribution of the light-sensitive cells. By providing such a light guide, a light beam can be spread in a substantially homogeneous manner over all the cells of the light-sensitive sensor.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A spectrometer comprising:
a lighting device configured to generate a light beam covering a wavelength band,
a probe configured so that the light beam coming from the lighting device interacts with a fluid to be analyzed, and
a spectrum analyzing device configured to receive the light beam after it has interacted with the fluid to be analyzed, and to provide measurements depending on a quality of light received for various ranges of wavelengths,
the spectrum analyzing device comprising a first light guide coupled to the probe and receiving the light beam after it has interacted with the fluid to be analyzed and diffusing it to a first set of light-sensitive cells through a first optical filtering device arranged to send each of the light-sensitive cells of at least one part of the set of light-sensitive cells, a part of the light beam covering a respective range of wavelengths included in the wavelength band, the first light guide having the shape of a plate made of a transparent material, receiving the light beam coming from the fluid to be analyzed by an edge of the plate and diffusing it by spreading it to an opposite edge of the plate opposite which the first filtering device and the first set of light-sensitive cells are placed.

2. The device according to claim 1, wherein the light beam produced by the lighting device covers a wavelength band between 700 nm and 1,100 nm.

3. The device according to claim 1, wherein the lighting device comprises several light-emitting components emitting light substantially in the same range of wavelengths.

4. The device according to claim 3, wherein the light-emitting components are light-emitting diodes.

5. The device according to claim 1, wherein the probe comprises an optical fiber illuminating light guide sending the light beam coming from the lighting device to the fluid to be analyzed, and an optical fiber collecting light guide coupled to the illuminating light guide and collecting at least partially the light beam having passed through the fluid to be analyzed and sending it to the spectrum analyzing device.

6. The device according to claim 5, wherein the collecting light guide comprises several collecting optical fibers spread around the illuminating light guide, and a reflector to send back the light beam after it has passed through the fluid to be analyzed to the collecting optical fibers through the fluid to be analyzed.

7. The device according to claim 6, wherein the reflector is produced so as to reflect each incident light ray of a light beam substantially in an opposite direction to that of the incident light ray with a slightly wider angle.

8. The device according to claim 7, wherein the reflector is of safety reflector type with retro-reflecting prisms or comprises transparent microbeads stuck onto a medium and having half of their surface turned toward the medium covered with a reflecting layer.

9. The device according to claim 6, wherein the reflector has the shape of a spherical shell centered substantially on the center of an output face of the illuminating light guide.

10. The device according to claim 6, wherein the probe comprises a converging lens arranged between the output of the illuminating light guide and the fluid to be analyzed.

11. The device according to claim 5, wherein the probe comprises a Y optical coupler to send the light beam at the output of the illuminating light guide into the fluid to be analyzed, and to send the light beam coming from the fluid to be analyzed into the collecting light guide, and a reflector to send back the light beam after it has passed through the fluid to be analyzed to the optical coupler through the fluid to be analyzed.

12. The device according to claim 11, wherein the reflector is produced so as to reflect each incident light ray of a light beam substantially in an opposite direction to that of the incident light ray.

13. The device according to claim 12, wherein the reflector is of safety reflector type with retro-reflecting prisms or comprises transparent microbeads stuck onto a medium and having half of their surface turned toward the medium covered with a reflecting layer.

14. The device according to claim 11, wherein the reflector has the shape of a spherical shell centered substantially on the center of an output face of the illuminating light guide.

15. The device according to claim 11, wherein the probe comprises a converging lens arranged between the coupler and the fluid to be analyzed.

16. The device according to claim 5, wherein the probe comprises a converging lens arranged between the output of the illuminating light guide and the fluid to be analyzed and a converging lens arranged between the collecting light guide and the fluid to be analyzed.

17. The device according to claim 1, wherein the collecting light guide is coupled to the first light guide to send it the light beam.

18. The device according to claim 1, wherein the spectrum analyzing device comprises a strip of photodetectors comprising the first set of light-sensitive cells, which is fixed onto the edge of the plate through the first filtering device.

19. The device according to claim 1, wherein the first filtering device comprises a filter of the spectrum transmission interference type linearly variable over its length.

20. The device according to claim 1, wherein the filtering device covers a wavelength band between 700 nm and 1,100 nm.

21. The device according to claim 1, wherein the spectrum analyzing device comprises a second light guide taking a part of the light beam directly at the output of the lighting device and sending the part of the light beam to a second set of light-sensitive cells through a second optical filtering device arranged to send each of the light-sensitive cells a part of the light beam covering a respective range of wavelengths included in the wavelength band.

22. The device according to claim 21, wherein the second light guide has the shape of a plate made of a transparent material, receiving a part of the light beam coming from the lighting device by an edge of the plate and diffusing it by spreading it to an opposite edge of the plate opposite which the second filtering device and the second set of light-sensitive cells are placed.

23. The device according to claim 22, comprising an optical fiber light guide coupled to the second light guide to send the light beam coming from the lighting device to the second light guide.

24. The device according to claim 21, wherein the spectrum analyzing device comprises a strip of photodetectors comprising the first and the second sets of light-sensitive cells, which is fixed onto the edge of the plates of the first and second light guides through the first and second filtering devices.

25. The device according to claim 21, wherein the second filtering device comprises a filter of the spectrum transmission interference type linearly variable over its length.

26. The device according to claim 1, wherein the lighting device comprises several light-emitting components each comprising an emitting surface and emitting light in various ranges of wavelengths included in the wavelength band, and a mixing optical component fixed onto the emitting surface of the light-emitting components, to combine the light flows emitted by the light-emitting components into a resulting light beam covering the wavelength band, and to guide the resulting light flow to the probe.

27. The device according to claim 26, wherein the mixing optical component has an input face receiving the light coming from the light-emitting components, an output face coupled to the lighting guide, and a shape having a substantially optimized revolution to focus and send as much light as possible from the light-emitting components to the probe.

28. The device according to claim 26, wherein the mixing optical component covers a light-emitting surface of each of the light-emitting components.

29. The device according to claim 26, wherein the mixing optical component is coupled by one or more optical fibers to a light-emitting surface of each of the light-emitting components.

* * * * *

UNITED STATES PATENT AND TRADEMARK OFFICE
CERTIFICATE OF CORRECTION

| | | |
|---|---|---|
| PATENT NO. | : 7,982,189 B2 | Page 1 of 1 |
| APPLICATION NO. | : 12/756497 | |
| DATED | : July 19, 2011 | |
| INVENTOR(S) | : Johan Fournel et al. | |

It is certified that error appears in the above-identified patent and that said Letters Patent is hereby corrected as shown below:

Column 2, line 7:
"minors" should read -- mirrors --;

Column 11, line 60:
"quality" should read -- quantity --.

Signed and Sealed this
Thirteenth Day of March, 2012

David J. Kappos
*Director of the United States Patent and Trademark Office*